United States Patent [19]
Levy et al.

[11] Patent Number: 5,800,249
[45] Date of Patent: Sep. 1, 1998

[54] FIBER SHAPER

[75] Inventors: Uri Levy, Rehovot; Joshua Degani, Jerusalem; Ytzhak Rozenberg, Tel Aviv; Ofer Braude, Ramat-Gan, all of Israel

[73] Assignee: Laser Industries, Ltd., Tel Aviv, Israel

[21] Appl. No.: 676,678

[22] Filed: Jul. 10, 1996

[51] Int. Cl.⁶ .................................................... B24B 1/00
[52] U.S. Cl. ............................ 451/41; 451/43; 451/44; 451/63; 451/212; 451/213; 451/221; 451/382
[58] Field of Search ............................ 451/41, 63, 382, 451/43, 44, 212, 213, 221

[56] References Cited

U.S. PATENT DOCUMENTS

| | | | |
|---|---|---|---|
| 4,272,926 | 6/1981 | Tamulevich | 451/286 |
| 4,492,060 | 1/1985 | Clark | 451/41 |
| 4,498,260 | 2/1985 | Doty | 451/365 |
| 5,683,290 | 11/1997 | Kanda et al. | 451/41 |

FOREIGN PATENT DOCUMENTS

| | | | |
|---|---|---|---|
| 63-102863 | 5/1988 | Japan | 451/241 |
| PCT/US93/ 09538 | 10/1993 | WIPO | |

*Primary Examiner*—Robert A. Rose
*Assistant Examiner*—George Nguyen
*Attorney, Agent, or Firm*—Cobrin Gittes & Samuel

[57] ABSTRACT

Reconditioning a fiber for laser applications by cleaving off its tip and shaping the cleaved end into a conical or pyramidal shape with a grinder. The cleaved end is grasped in a fiber holder. The grinder is driven, e.g., to rotate. The fiber holder is moved relative to the grinder to bring it into contact with the moving grinder. The fiber holder may be rotated during the contact. Preferably, the axis of symmetry of the fiber is substantially parallel to the plane of rotation of the grinder to effect tangential grinding.

11 Claims, 6 Drawing Sheets

FIBER SHAPER

BACKGROUND OF THE INVENTION

1. Field of the Invention

The present invention relates to shaping tips of fibers for use with lasers. Such shaped tips are useful for medical applications.

2. Discussion of Related Art

Many medical applications call for the use of fibers with high power lasers. Over extended use, the tips of these fibers deteriorate through distortion or contamination. Conventionally, used fibers whose tips have become distorted, dirty or otherwise lost their original shape and mechanical integrity are thrown away and replaced by a new, factory prepared fiber. Such a practice is costly.

SUMMARY OF THE INVENTION

One aspect of the invention resides in an apparatus that shapes fibers. The apparatus includes a grinder, a fiber holder that grasps a fiber so that a tip of the fiber protrudes from the fiber holder, and an advancer that moves the fiber holder relative to the grinder to selectively bring the protruding tip of the fiber into and out of contact with the grinder. The tip is then shaped to have a conical or pyramidal shape with diffusing edges that scatter light reaching it from the laser in all directions so that power density at the tip is high but falls off rapidly away from the tip.

Another aspect of the invention resides in a method of shaping a fiber tip to have a conical or pyramidal shape suitable for tissue cutting that is preferably strong enough to resist mechanical breakage while cutting and is sharp rather than blunt for better cutting performance. The method includes the steps of cleaving an end of the fiber, holding the fiber with a fiber holder, advancing the fiber holder so that a tip of the fiber comes into contact with a grinding surface of a grinder, shaping the fiber tip, and releasing the fiber when done, and possibly stripping the cladding and/or jacket layers of the fiber.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 1:
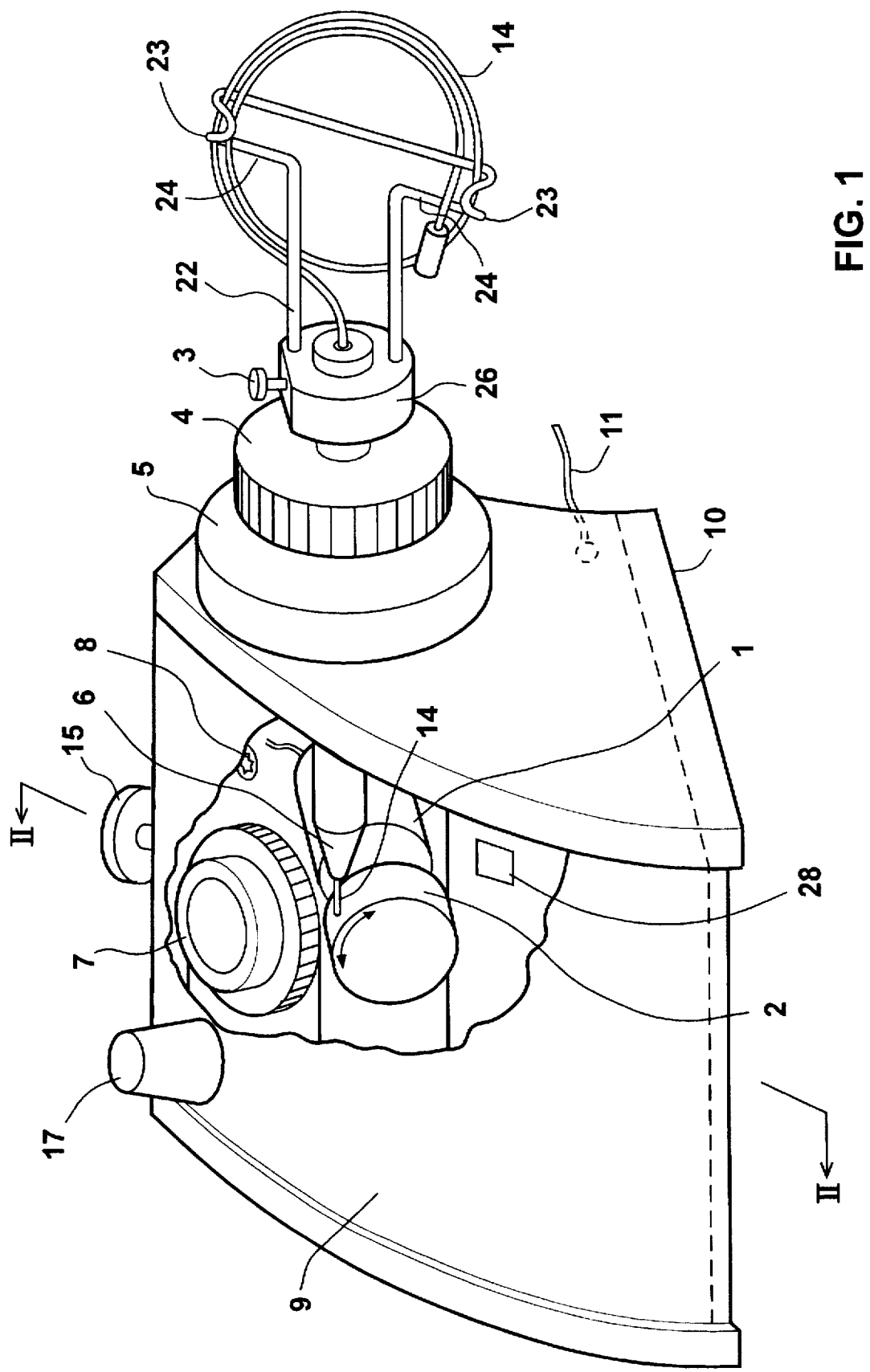
FIG. 1 is a perspective view, partially broken to reveal the inside components, of a fiber shaper apparatus in accordance with the invention.
Figure 2:
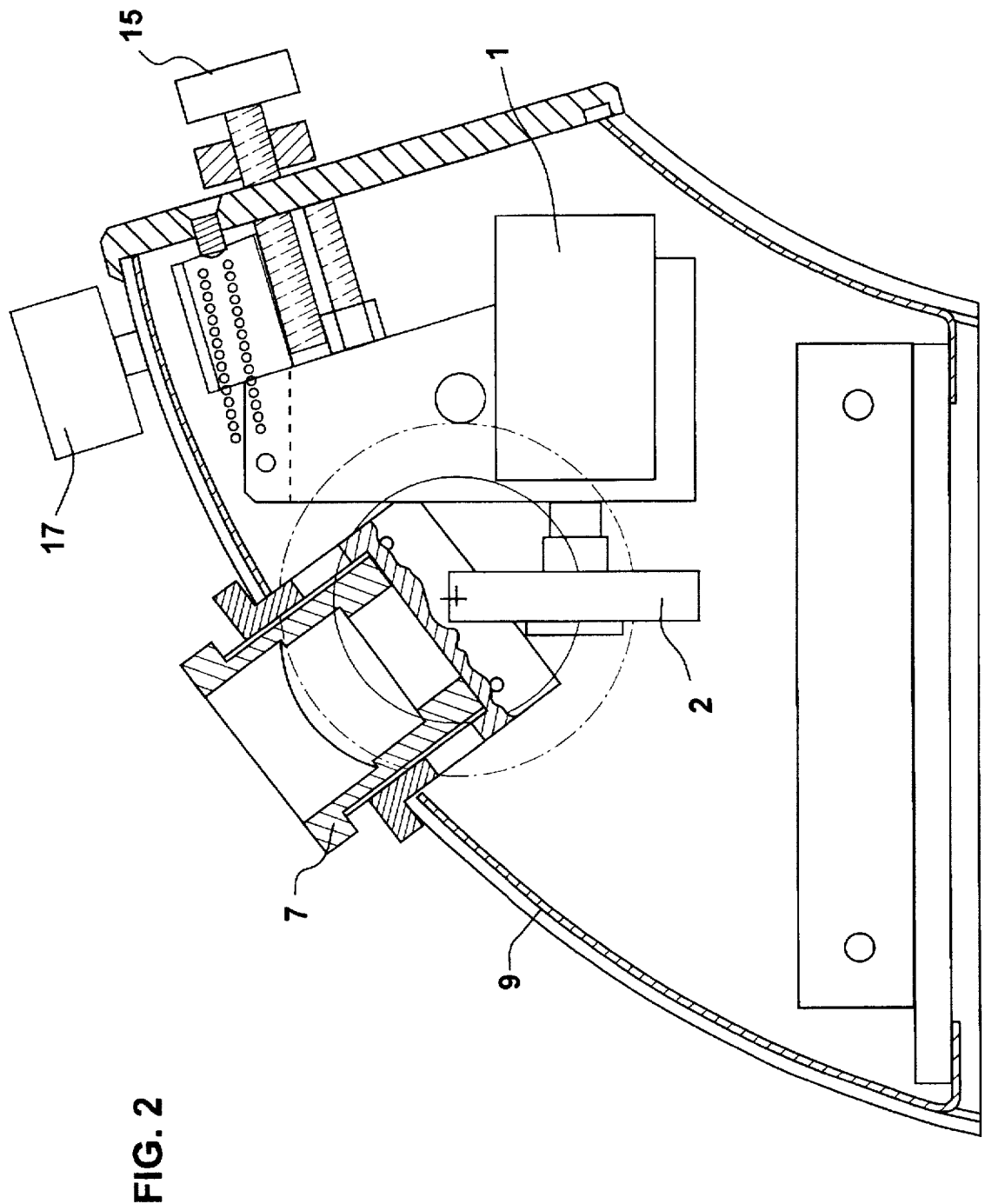
FIG. 2 is a cross-section along 2—2 of FIG. 1.
Figure 3:
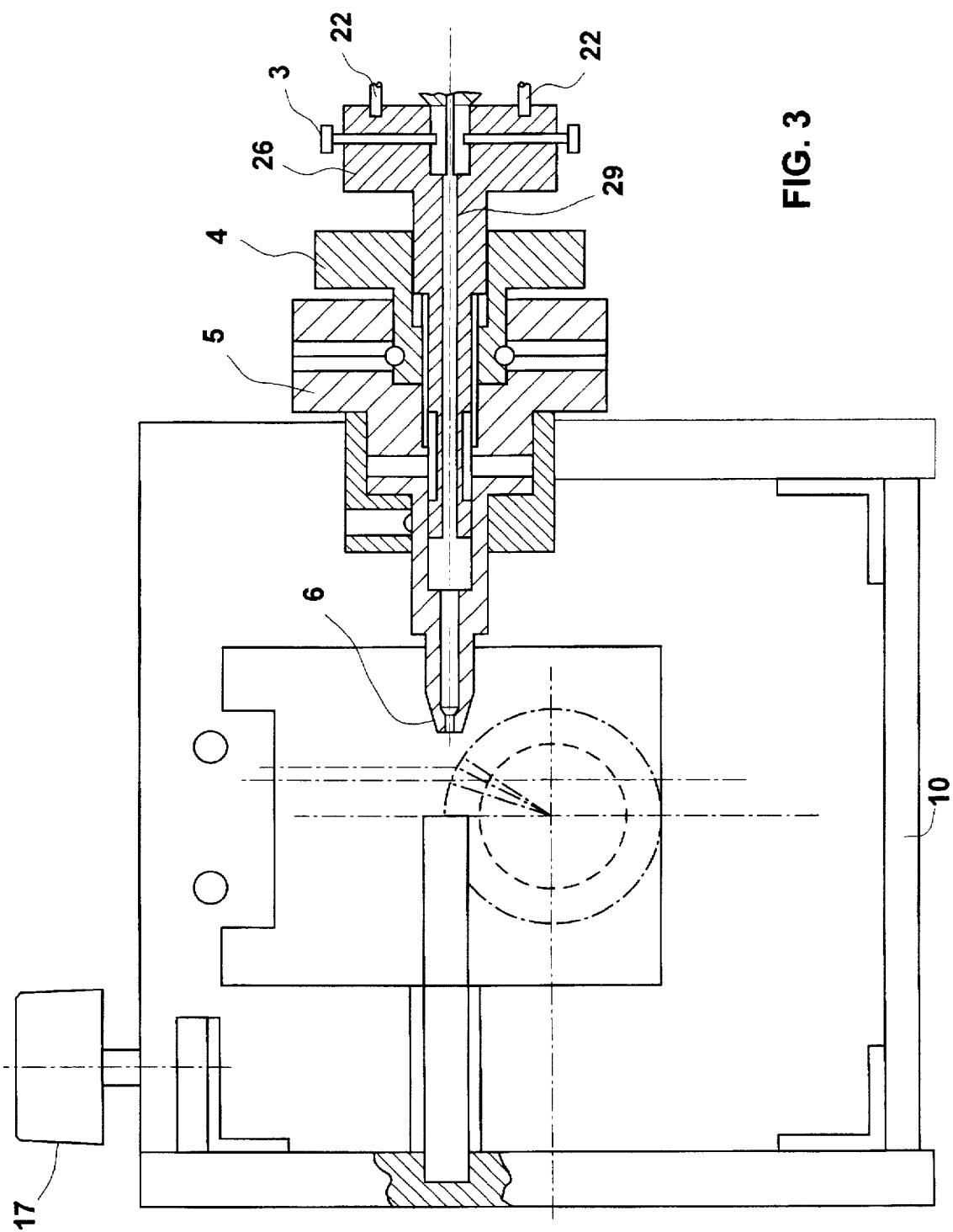
FIG. 3 is a longitudinal cross-section of FIG. 1.

FIGS. 1–3 show the fiber shaper apparatus in accordance with the invention. The apparatus includes a driver or motor 1, a grinding stone 2 (or grinding disc, polishing stone or polishing disc), a fiber fastening knob 3, a fiber advancing knob 4, a fiber rotating knob 5, fiber holding lips 6, a magnifying lens 7, illuminating lamps 8, a cover 9, a base 10, a power cord 11, a y-translation knob 15 and a speed control knob 17. The motor 1 drives the grinding stone 2 to rotate.

Also shown is the fiber 14 to be shaped. Referring briefly to FIGS. 4–7, the fiber 14 may be a composite 18 of an outer jacket 19, an inner cladding layer 20 and a fiber core 21. The fiber core 21 is preferably composed of silica glass and the jacket and cladding layer are made of plastic.

As can be seen in FIG. 1, the fiber 14 is supported in a fiber-support frame 22 to prevent the fiber from dangling. As shown, the fiber 14 is coiled and fitted between the bent ends 23 of arms 24. The frame 22 has legs held in grooves of a fiber holder 26. There is also an on-off switch 28 to actuate or shut off the motor 1, and/or lamps 8.

As may be appreciated from FIGS. 4–7, conical-tip fibers or pyramidal-tip fibers are to be produced with the fiber shaper apparatus of FIG. 1. When used in medical applications, the conical or pyramidal shaped tip is light-diffusive and hot and is useful for cutting and coagulating soft tissues. When laser light is guided to the tip, the tip gets hot because the power density is relatively high. As the laser light exits the tip, it scatters rapidly in all directions through diffusing edges so that the power density falls off quickly away from the tip. In this manner, the tissue that is away from the immediate proximity of the tip barely gets hot. As a result, the surgeon using the conical tip can cut and coagulate where desired without having to worry about possible thermal damage to neighboring organs.

Figure 4:
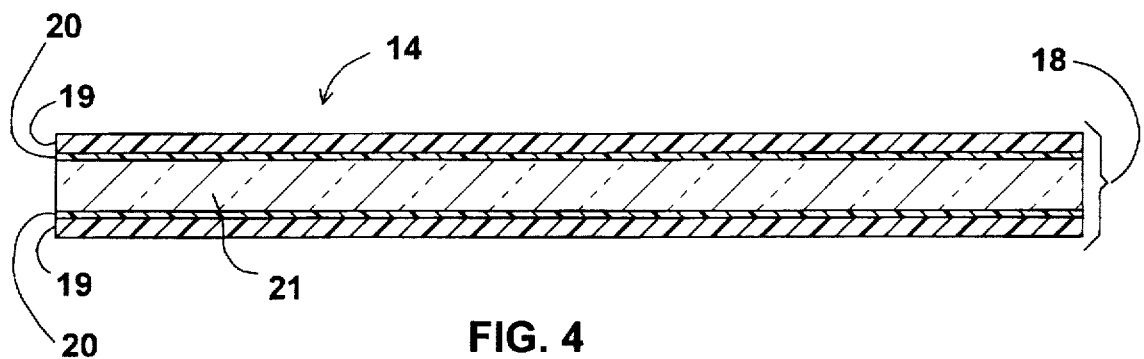
FIG. 4 is a schematic representation of a cleaved fiber prior to shaping in the apparatus of FIG. 1.

Initially, the worn tip of the fiber to be reconditioned is cleaved off, leaving an unshaped end as shown in FIG. 4. It is preferred that the operator rest the tail of the fiber on the fiber support frame 22 in a coiled manner as shown. In this manner, when the fiber tip is rotated during the shaping process, the whole fiber is rotated with it and the fiber rotation can go on smoothly and continuously with no obstruction or resistance from the tail end.

In accordance with the preferred embodiment, the motor 1 has a power of 5 to 25 watts, AC or DC, 1000 to 5000 RPM (revolutions per minute). The grinding stone 2 has a diameter of 20 to 50 mm and a thickness of 5 to 15 mm, fine grain. The fiber advancing knob 4 has an advancing amplitude of 5 to 20 mm, preferably with low screw-rotation so that the advancing operation may be done with one hand without needing to simultaneously counter-hold the rotation knob 5. The cover 9 and the base 10 are sufficiently sturdy to provide stability and safety throughout the shaping procedure. The cover 9 may be lifted by the operator for cleaning and for replacement of the grinding stone 2 or the lamp 8.

Figure 5:
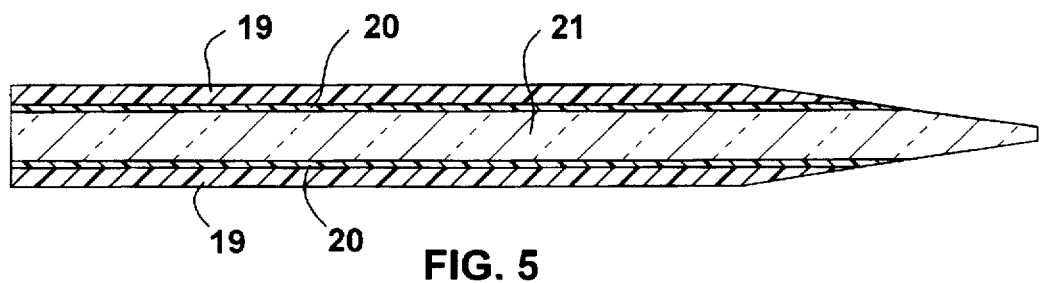
FIG. 5 is a schematic representation of the fiber of FIG. 4 after shaping by the apparatus of FIG. 1.
Figure 6:
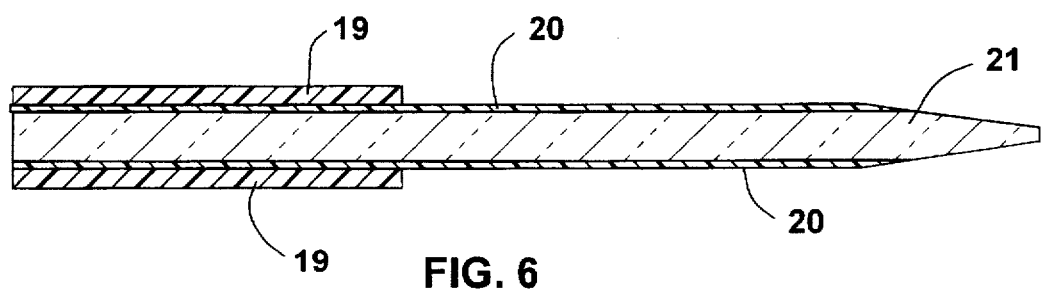
FIG. 6 is the same as FIG. 5 except that the jacket was stripped prior to or after shaping.
Figure 7:
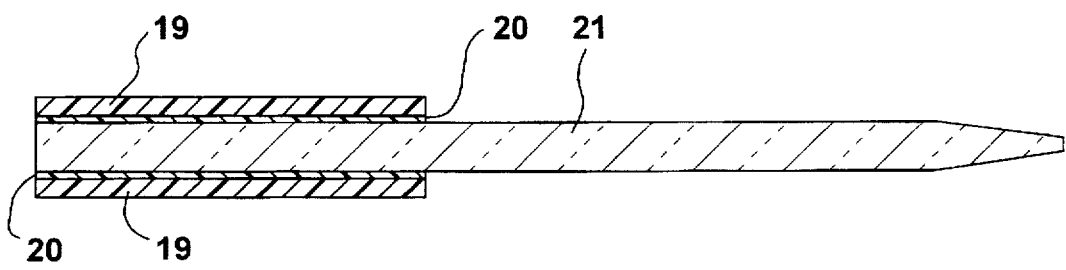
FIG. 7 is the same as FIG. 6 except that the jacket and cladding layer were stripped after or prior to shaping.

When the grinding is done, the jacket and cladding may remain as shown in FIG. 5, the jacket alone may be stripped off as shown in FIG. 6 or both the jacket and cladding may be stripped off as shown in FIG. 7. Alternatively, the stripping may be done prior to the shaping, but the reverse is preferred to avoid weakening the tip prior to shaping and to make it easier to shape the tip during grinding.

The operation is as follows.

First, the operator turns on the motor 1 by pressing the switch 28. If lamp lights are present, they also are turned on with the motor as part of the same circuitry actuated by pressing the switch 28 to on. Next, the operator inserts the fiber 18 through the central aperture 29 of the fiber holder knob 26 and gently through the holding lips 6 until the fiber tip is in the proximity of the grinder as determined by looking through the lens 7, or until a grounding sound is heard because of the tip of the fiber making contact with the grinding surface of the grinder. The operator then tightens the fiber 14 by holding the fiber advancing knob 4 and rotating the fiber fastening knob 3 clockwise.

Next, the operator looks through the magnifying lens 7 and, by rotating the fiber rotating knob 5 in the clockwise or counterclockwise directions, causes the fiber to rotate clockwise or counterclockwise about its own axis of symmetry. While this rotation is being done, the grinding stone 2 is grinding the fiber tip into a conical shape.

In the event that the tip breaks or the tip is too trapezoidal, the operator can rotate the fiber advancing knob 4 clockwise to gradually advance the fiber. Once the advancement is complete, rotation with the fiber rotating knob 5 resumes. The operator may continue this advance-rotate-advance-rotate sequence until the shaping of the tip is complete and satisfactory as viewed by the operator through the magnifying lens 7.

When done, removal of the fiber 14 is done by turning the advancing knob in a reverse direction. The operator rotates fiber advancing knob 4 counter clockwise to withdraw the fiber 14 from contact with the grinding stone 2. The operator then rotates the fiber fastening knob 3 counter clockwise to release the fiber 14 from the fiber holder 26. Thereafter, the operator pulls the fiber 14 out of the apparatus. The next fiber may now be inserted for shaping or the motor may be turned off by pressing the switch 28 to off.

The entire shaping process takes a few minutes and, with practice, under one minute.

An important aspect of the preferred embodiment is reliance on tangential grinding. Tangential grinding takes place where the fiber axis of symmetry lies substantially parallel to the plane of rotation of the grinding stone. In this manner, the stone-fiber friction force is relatively small and is mostly pooling, i.e., trying to stretch the fiber along the fiber's axis. The fiber is strong and inflexible in the direction of its axis.

Tangential grinding differs from angled grinding and particularly from transverse grinding with respect to stability. In transverse grinding, the forces are in the directions along which the fiber is flexible. The result of these (usually larger) forces is instability of the tip position during grinding. This in turn causes poor grinding results, producing rough and uneven surface shapes and greatly increases the chance of tip-breakage during the grinding process.

The configuration of the invention as described is based on using a cylindrical grinding stone, tangential fiber grinding and manually rotating the fiber around its axis of symmetry. Other configurations are envisioned such as a trapezoidal grinding stone, transverse grinding and planetary fiber motion around the stone. Another configuration may be a hollow conical grinding stone with fiber advancement but no rotation. In short, any type of movement of a fiber into contact with a grinding surface capable of shaping the tip into a desired shape is envisioned where the grinding surface is driven to move either in a rotary, planetary or linear fashion.

Sometimes the operator may desire a flat, diffused surface as a result of the fiber grinding. This diffused surface would provide a different effect on tissue as laser light exits from the tip. Alternatively, the realization of the diffused surface is suitable as a preparation for polishing. A special port is provided to provide for a head-on approach to obtain a flat transverse diffusing surface or, if a conical tip fiber is inserted through this special port, to obtain a truncated-cone (trapezoidal) shape.

Figure 8:
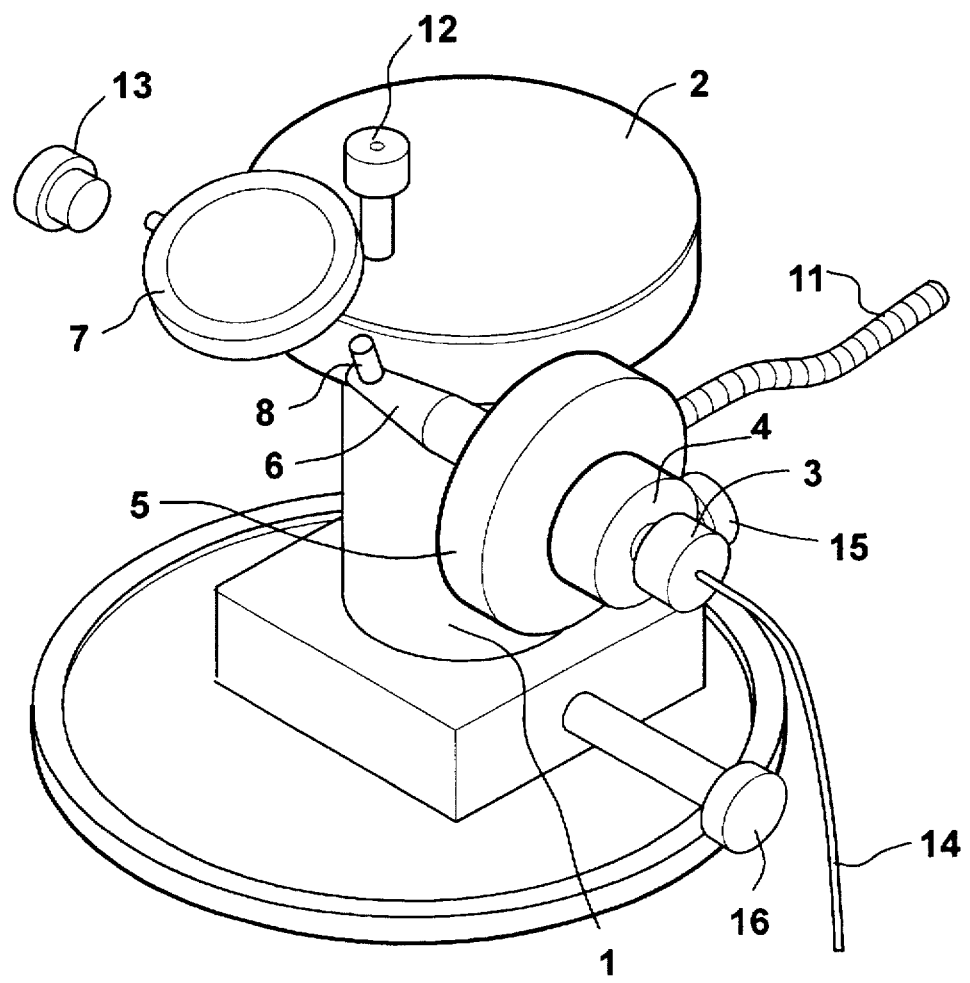
FIG. 8 is a perspective view of a further embodiment with the outer cover removed.
Figure 9:
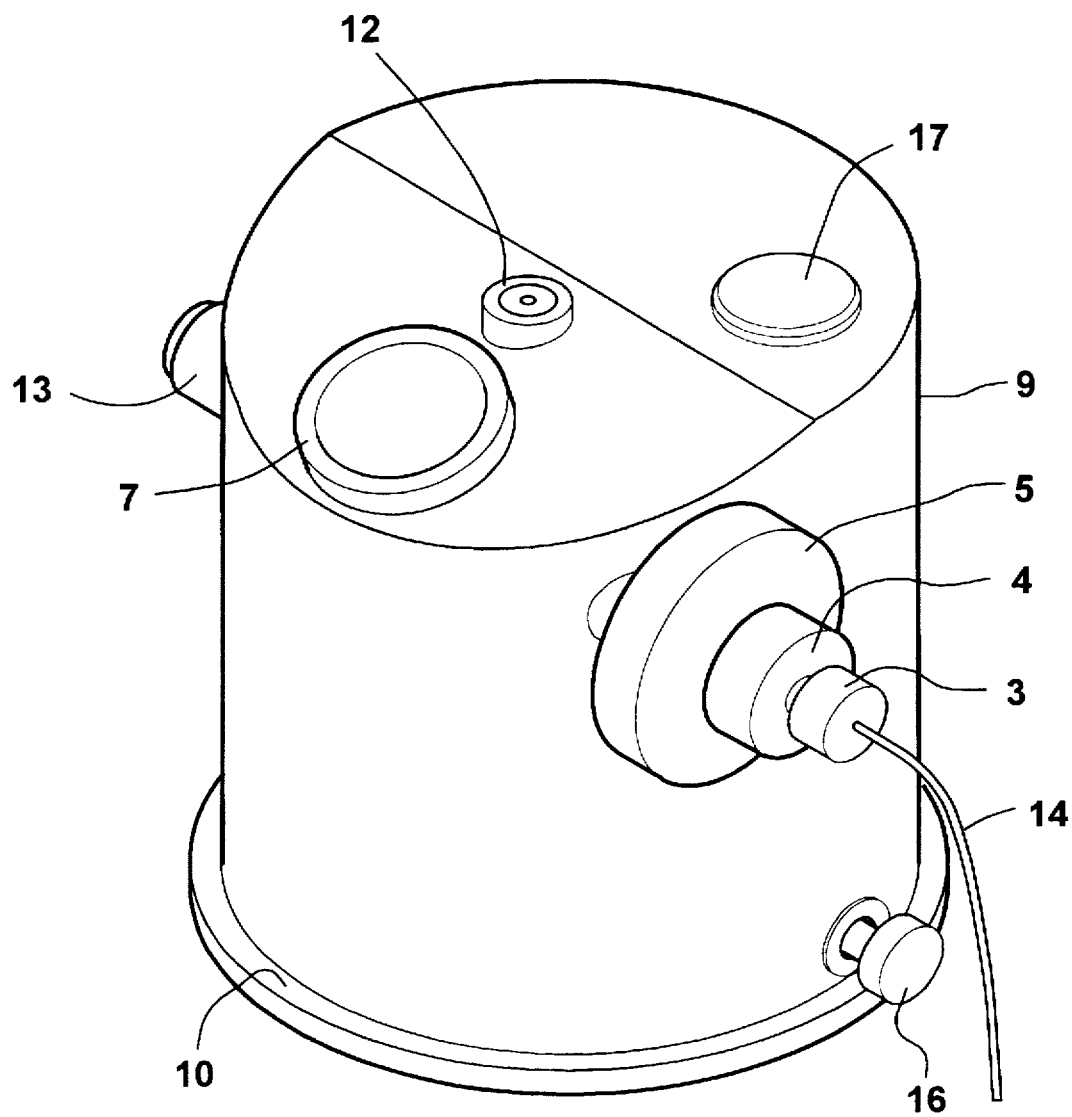
FIG. 9 is a perspective view of the FIG. 8 embodiment with the outer cover.

This special port is shown in the embodiment of FIG. 8, i.e., as port 12. This embodiment is a variation of that of FIGS. 1–3 in that instead of the cover 9 being curved, it is straight. FIG. 8 makes provision for a left handed port 13, a y-translation knob 15 and a z-translation knob 16. The remaining components are numbered the same as their counterparts in FIGS. 1–3.

The knobs 3, 4, 5 and lips 6 may be pulled out of the right port (where they are located in FIG. 8) and inserted into the left handed port 13. Together with inverting the motor sense of rotation, these provisions allow for convenient grinding by left-handed persons. Such a left handed port could also be provided in the embodiment of FIG. 1 for insertion of the fiber holder 26 and knobs 3, 4, 5 and lips 6.

The y-translation knob 15 is used to move the motor 1 and the grinding stone 2 to effect relative movement with respect to the fiber 18 in a direction perpendicular to the axis of the fiber to alter the head-angle of the tip to be grounded conical or trapezoidal. In this manner, the cone angle may be adjusted.

The z-translation knob 16 is used to move the motor 1 and the grinding stone 2 perpendicular to the plane defined by the stone. The contact edge of the grinding stone may be considered as composed of a plurality of adjacent rings. Moving the z-translation knob 16 permits a different ring of the grinding stone to come into contact with fiber, i.e., one that is more "fresh" and less worn than the current one.

To gently grind small diameter fibers at low speed or head-on at lower speeds, a speed control knob 17 is provided to, for instance, vary the resistance of a variable resistor governing the speed control of the motor 1. While a power cord 11 is shown, the shaper apparatus may operate on a battery.

Commonly used medical fibers fall within the range between 400 microns and 1000 microns. To handle these, it is preferred that two elements of the lips be provided; the first is for holding the 400 and 600 micron fibers while the second is for holding the 800 and 1000 micron fibers. The lips are replaced by unscrewing the unsuitable type and screwing instead the suitable type.

There may be situations where rotating the fiber during grinding is not required, such as where cutting is only to be done in one direction. In this case the ability to rotate the fiber is unnecessary. Alternatively, two or more grinders could be provided offset from each other by 90 degrees in which case the fiber may be shaped on two or more sides without the need for rotating the fiber mechanically during grinding since the fiber would merely be moved to contact the appropriate grinder.

While the foregoing description and drawings represent the preferred embodiments of the present invention, it will be understood that various changes and modifications may be made without departing from the spirit and scope of the present invention.

What is claimed is:

1. An apparatus for shaping the tip of a fiber, comprising:
   a grinder including a grinding surface, said grinder being operable in an active mode and inoperable in an inactive mode;
   a fiber holder for grasping a portion of a fiber, so that at least a tip of the fiber protrudes from the fiber holder;
   an advancer operable to move the fiber holder relative to said grinder so as to selectively bring at least the tip of the fiber into and out of contact with the grinding surface; and a rotator operable to rotate said fiber holder about an axis, the advancer and the rotator being operable when the grinder is in the active mode, wherein said rotator and advancer each have knobs movable independent of each other and nested one in the other.

2. An apparatus for shaping the tip of a fiber, comprising:

a grinder including a grinding surface, said grinder being operable in an active mode and inoperable in an inactive mode;

a fiber holder for grasping a portion of a fiber, so that at least a tip of the fiber protrudes from the fiber holder;

an advancer operable to move the fiber holder relative to said grinder so as to selectively bring at least the tip of the fiber into and out of contact with the grinding surface; and a rotator operable to rotate said fiber holder about an axis, the advancer and the rotator being operable when the grinder is in the active mode, wherein said grinder includes a stone, further comprising a driver that drives said stone to rotate so that rotation is within a plane, said fiber holder grasping said fiber such that a tip of the fiber, upon advancement into contact with said grinder by said advancer, has an axis of symmetry that lies substantially parallel to said plane to thereby provide for tangential grinding.

3. A method to shape the tip of a fiber, comprising the steps of:

grasping a fiber with a fiber holder so that a tip of the fiber protrudes from the fiber holder;

activating a grinder, said grinder including a grinding surface;

moving the fiber holder relative to the grinder, at least while said grinder is activated, so as to bring the tip and the tangential face of the fiber into and out of contact with the grinding surface, the grinding surface moving so that the contact causes grinding of the tip and the tangential face of the fiber; and rotating the fiber holder, whereby the fiber rotates, whereby the tip is shaped into a desired form by grinding in response to the contact, further comprising driving said grinding surface to rotate so that rotation is within a plane, said fiber holder grasping said fiber such that a tip of the fiber, upon making contact with said grinding surface, has an axis of symmetry that lies substantially parallel to said plane to thereby provide for tangential grinding.

4. A method to shape the tip of a fiber, comprising the steps of:

grasping a fiber with a fiber holder so that a tip of the fiber protrudes from the fiber holder;

activating a grinder, said grinder including a grinding surface;

moving the fiber holder relative to the grinder, at least while said grinder is activated, so as to bring the tip and the tangential face of the fiber into and out of contact with the grinding surface, the grinding surface moving so that the contact causes grinding of the tip and the tangential face of the fiber; and rotating the fiber holder, whereby the fiber rotates, whereby the tip is shaped into a desired form by grinding in response to the contact, wherein the grinding surface is on a body of the grinder, the moving of the grinding surface being carried out by rotation of the body, the step of shaping including tangentially grinding the tip of the fiber with the grinder during which an axis of symmetry of the fiber is substantially parallel to a plane of the rotation.

5. A method to shape the tip of a fiber, comprising the steps of:

grasping a fiber with a fiber holder so that a tip of the fiber protrudes from the fiber holder;

activating a grinder, said grinder including a grinding surface;

moving the fiber holder relative to the grinder, at least while said grinder is activated, so as to bring the tip and the tangential face of the fiber into and out of contact with the grinding surface, the grinding surface moving so that the contact causes grinding of the tip and the tangential face of the fiber, and rotating the fiber holder, whereby the fiber rotates, whereby the tip is shaped into a desired form by grinding in response to the contact, wherein the grinding surface is on a body of the grinder, the moving of the grinding surface being carried out by rotation of the body, the step of shaping including angled grinding of the tip of the fiber during which an axis of symmetry of the fiber is in a relative position with respect to the grinder so as to be other than substantially parallel to a plane of the rotation.

6. A method as in claim 5, wherein the angled grinding is effected transverse to the plane.

7. A method as in claim 5, wherein the step of moving includes varying an angular approach of the fiber relative to the grinder.

8. An apparatus for shaping the tip of a fiber, comprising:

a grinder including a grinding surface, said grinder being operable in an active mode and inoperable in an inactive mode;

means for holding a fiber such that at least a portion of said fiber extends therefrom for contact with the grinding surface, the fiber having an axis; and a rotator operable to rotate said fiber holder about the axis, the rotator being operable when the grinder is in the active mode, wherein said means for holding the fiber include a bore for slidably receiving the fiber and means for clamping a portion of the fiber within the bore, and means for moving the fiber along X and Y axes, and the grinder includes means for moving the grinding surface in a direction substantially parallel to the Z axis, said Z axis substantially normal to said X and Y axes.

9. The apparatus of claim 8, wherein said holding means and said rotator are movable independent of each other.

10. An apparatus for shaping the tip of a fiber, comprising:

a grinder including a grinding surface, said grinder being operable in an active mode and inoperable in an inactive mode, means for holding a fiber such that at least a portion of said fiber extends therefrom for contact with the grinding surface, the fiber having an axis; and a rotator operable to rotate said fiber holder about the axis, the rotator being operable when the grinder is in the active mode, additionally comprising a fiber support frame projecting from said fiber holding means for supporting a portion of the fiber.

11. An apparatus as in claim 10, wherein said support frame includes two arms extending in opposite directions, said arms having ends projecting is a common direction different from that to which said arms extend.

* * * * *